Figure 1:
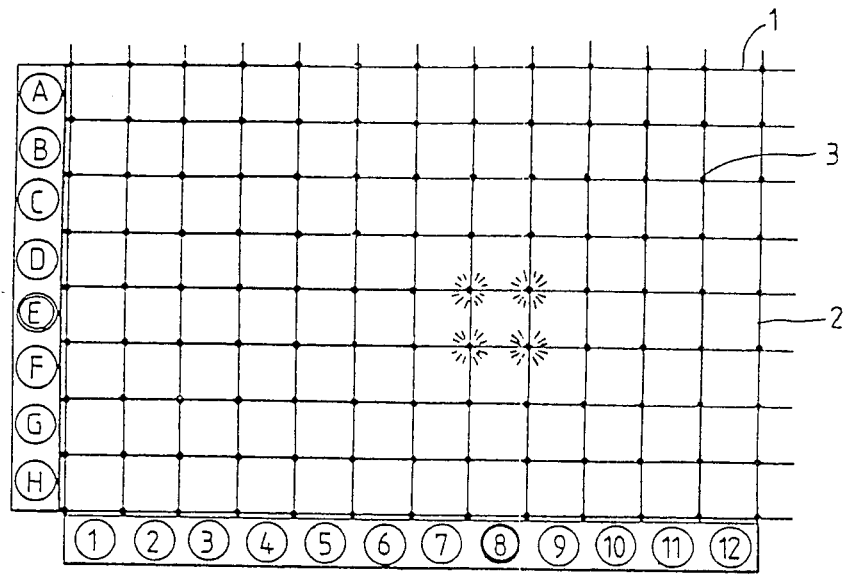

United States Patent [19]

Chidlow et al.

[11] Patent Number: 4,563,096

[45] Date of Patent: Jan. 7, 1986

[54] APPARATUS FOR ASSISTING THE VISUAL ASSESSMENT OF TEST OBJECTS HAVING MULTIVARIATE VISIBLE CHARACTERISTICS, AND ITS USE

[75] Inventors: John W. Chidlow, Basingstoke, England; Jan Van Duijn; Jan Siebesma, both of Vlaardingen, Netherlands

[73] Assignee: Internationale Octrooi Maatschappij "Octropa" B.V., Rotterdam, Netherlands

[21] Appl. No.: 339,443

[22] PCT Filed: May 8, 1981

[86] PCT No.: PCT/GB81/00083

§ 371 Date: Jan. 8, 1982

§ 102(e) Date: Jan. 8, 1982

[87] PCT Pub. No.: WO81/03223

PCT Pub. Date: Nov. 12, 1981

[30] Foreign Application Priority Data

May 9, 1980 [GB] United Kingdom ................. 8015430

[51] Int. Cl.$^4$ ............................................ G01N 21/01
[52] U.S. Cl. ..................................... 356/440; 356/244
[58] Field of Search ............... 356/436, 440, 441, 244; 435/289, 293

[56] References Cited

U.S. PATENT DOCUMENTS 4,252,897  2/1981  Axford et al. ........................ 435/289
4,367,043  1/1983  Sweet et al. ..................... 356/244 X

FOREIGN PATENT DOCUMENTS 2014300  8/1979  United Kingdom .
2014305  8/1979  United Kingdom .

OTHER PUBLICATIONS

Proceedings of the IEEE, vol. 66, No. 2, Published in Feb. 1978, (New York, US), W. Randle et al.: "Microprocessors in Instrumentation", pp. 172–181, See in Particular pp. 172–173.

Primary Examiner—Rodney B. Bovernick
Attorney, Agent, or Firm—Cushman, Darby & Cushman

[57] ABSTRACT

Apparatus for use in and for assisting the visual assessment by a human operator of test objects, in each of which test objects a multiplicity of test locations each has one or more visible characteristics capable of exhibiting any one of a number of conditions to be assessed (e.g. a prepared microtiter plate or tray having an array of test locations or wells in which a series of microbial cultures or biological or chemical tests has been carried out leading to results to be optically or visually assessed, e.g. in terms of turbidity and/or color), the apparatus comprising: (a) means for illuminating each of the test locations of the test object (either with sufficient light to enable the operator to see and assess the test location against a background of darkness, or with an indicator light sufficient to draw the operator's attention to the test location against a general background light); (b) means for positively locating the test object in registration with the illuminating means; (c) means for controlling the illuminating means so that all of the test locations can be selectively illuminated, either singly or in groups, according to a program-determined sequence; and (d) means to enable the operator manually to actuate and control stepping along the sequence.

6 Claims, 2 Drawing Figures

APPARATUS FOR ASSISTING THE VISUAL ASSESSMENT OF TEST OBJECTS HAVING MULTIVARIATE VISIBLE CHARACTERISTICS, AND ITS USE

This invention concerns apparatus for assisting the visual assessment of test objects having multivariate visible characteristics, and processes in which it is used.

Many kinds of testing procedures used in clinical laboratory practice and in manufacturing industry result in complex text objects with a multiplicity of spots or zones: their appearance has to be interpreted in order to obtain the test result. Fully automatic reading apparatus can be impracticable to provide, because in many cases the skill of an operator's trained eye cannot yet be mechanically initiated. On the other hand the reading by a human operator of a large number of items is a process frequently accompanied by error. This can be a source of danger where the test results are used to determine the course of medical therapy or the safe conduct of manufacturing processes. Therefore there is a need for apparatus which can ease the task of a human operator and allow a reduction in the opportunities for mistakes in reading.

According to the invention, this is provided in the form of apparatus for use in and for assisting the visual assessment by a human operator of test objects, in each of which test objects a multiplicity of test locations each has one or more visible characteristics capable of exhibiting any one of a number of conditions to be assessed, the apparatus comprising:

(a) means for positively locating the test object in registration with selective illuminating means;

(b) means for illuminating selected test locations of the test object, (either with sufficient light to enable the operator to see and assess the test location against a background of darkness, or with indicator light sufficient to draw the operator's attention to the test location against a general background light);

(c) means for controlling the illuminating means so that the test locations can be selectively illuminated either singly or in groups, according to a program-determined sequence;

(d) means to enable the operator manually to actuate and control stepping along the sequence;

(e) means arranged for actuation by the operator for recording and storing data input corresponding to the operator's visual assessment of the selectively illuminated location or locations;

(f) means for presenting to the operator a visual check display corresponding to the data input recorded in respect of the test locations under illumination to enable the operator to check the correctness of the data recorded by visually comparing the display with the test location.

The apparatus has particular application for example to the visual assessment of test objects in which a multiplicity of locations each has one or more visible characteristics which are capable of exhibiting any one of a number of conditions, and which may form a pattern capable of interpretative recognition. For example, one type of such a test object is a plate or tray having a plurality of areas each of which is capable of exhibiting visually detectable turbidity, or transparency, or degrees of turbidity. Another type of such a test object is a plate or tray having a plurality of areas each of which is capable of exhibiting a colour, or lack of colour, or degrees of colour, or any one of a number of different colours.

Such test objects can for example be produced as a result of carrying out test or assay routines of chemical, biochemical, biological, microbiological or other kinds upon materials for analysis, using for example arrays of prepared test reagents. The purpose of such tests and assay routines can variously be to quantitate or detect qualitatively any of a variety of constituents, properties or attributes of such materials for analysis. Materials which can be analysed in such ways include for example samples derived from chemical processes or biological sources or derivatives thereof. Among such materials are for example blood, urine, bodily secretions and internal fluids, (e.g. faecal material, spinal fluid, amniotic fluid), sera and antisera, microbial cultures and products thereof, chemical process samples, and derivatives thereof.

Among the kinds of test objects that can be produced in the course of testing or assaying such materials are for example a plate or tray carrying an array of areas or wells at or in a plurality of which a test or assay has been carried out, or at or in which a detectable material may be present to a variable extent or not at all.

For example, certain such test objects are multi-well plates, in each well of which there is present a microbial inoculate or culture which has developed (or failed to develop) in the presence of materials which can possibly affect its growth, e.g. antimicrobial materials or growth promoters. The degree of development or its lack can be indicated by turbidity or transparency, or colour development or its lack. Prepared plates of this kind can be for example for the determination of minimum inhibitory concentrations of selected antimicrobial materials, and can then incorporate series of wells (e.g. 12×8 rows), containing serial dilutions of selected antimicrobials, so that inhibitory concentrations can be assessed by comparison between the number and identity of wells in which growth and turbidity or colour develop, and the contents of the wells. Other prepared plates of this kind can be for example for the identification of micro-organisms, and can then incorporate wells containing possibly growth-affecting (e.g. growth-supporting) substances in (e.g. otherwise insufficient) culture media, and/or substances which can possibly be acted on by the organisms to be identified so as to produce detectable, e.g. coloured, products.

Further test objects can for example be trays having arrays of wells each containing eluate of a segment of the products of chemical separation methods, e.g. of a one- or two-dimensional chromatogram, or detectable derivatives thereof, or the test object can be a plate containing the separation medium itself with detectable materials located at a plurality of places thereon, e.g. a chromatogram.

According to the invention the inspection for the purpose of visual assessment, and the assessment itself, of such test objects can be facilitated by an arrangement for selectively illuminating zones or locations of the test object according to a controlled sequence. The test object is placed in an inspection position where it can be seen by the operator in registration with the illuminating arrangement. Conveniently, the controlled sequence can be triggered, for example its individual steps actuated, by the operator using a suitable manual control when he has assessed the test zone for the time being under illumination. Such an arrangement is convenient for the operator especially when large numbers of test objects have to be scanned, since it helps to minimise operator errors which may occur, e.g. by observing one particular zone twice and omitting to look at another zone, when a sequence of zones has to be inspected and an assessment of each redorded.

This arrangement can comprise an array of individually controllable light sources, and very advantageously in certain embodiments an array of light sources each comprising a controllable light-generator, such as a light-emitting diode, arranged for selective illumination of zones of the test objects. An advantage of this type of light source arrangement lies in the very sharp localised selective illumination (e.g. spots or lines adjacent the test zones) that can be achieved. These light sources can either give enough light for the operator to see the appropriate test zone, or else they can merely indicate the zone, in which case background light can be provided for the operator to see by while he inspects the test zone.

In certain convenient embodiments the test objects can be substantially flat apart from irregularity due to wells and the like, and can be translucent (apart from any opacity constituting the variable optical conditions for inspection and assessment) and the array of light sources can then be arranged so that the test object is selectively illuminated when placed against them or spaced from them and seen directly or indirectly by the user against a background of the array light sources. For example the light sources, e.g. light-emitting diodes, can be embedded in a transparent plate to overlie or support the trays or other test objects to be viewed.

The array of light sources can for example form a pattern of dots or lines when illuminated, forming for example a grid of rectangular or square zones to which the user's attention can be directed by selective illumination. For example, selective illumination of four points at the corners of a rectangular zone of a test object can direct the user's attention to the conditions within that zone: numbers of such zones forming rows, columns, or larger areas can also be selectively indicated.

The control for this selective illumination can most conveniently be achieved by any suitable multiple switching device with sufficient flexibility of control, such as a small digital computer, with each light source individually addressable by the computer. It is especially convenient here to provide additional checking facilities by means of such a computer, so that in the limit the fatiguing interpretative tasks required of the human user are reduced, and with them the likelihood of errors.

According to the invention, therefore, there is also provided an arrangement for assisting the visual assessment of test objects in which a multiplicity of locations each has one or more visible characteristics capable of exhibiting any one of a number of conditions, comprising means for selectively illuminating zones or locations of the test object according to a controlled sequence, means for recording and storing data input corresponding to the user's visual assessment of the selectively illuminated zone or location, and means for presenting to the user a visible check on the correctness of the data input recorded in respect of the assessment.

By the use of a small digital computer, and for example a visual display unit, a check can be presented to the user in the form for example of a visible reproduction of the condition of the zone or location corresponding to the data recorded in respect of the assessment. This visible reproduction can take the form of an image or diagram of the zone, in which case it can offer a most useful null-difference check. In using such an arrangement, the user assesses the illuminated zone, records data corresponding to the assessment, and is then presented with a visible image or diagram. If the user's assessment and recording operation was correct, the image or diagram corresponds to the assessed zone of the test object, otherwise not, and the user is alerted to perform a reassessment.

With such an embodiment, conventional programming can be used to ensure any of the following operational features according to need: that index data are recorded in respect of the identity of the test objects, that all relevant zones of the test object are in turn selectively illuminated for the recording of data corresponding to their assessment, that index data are recorded in respect of the identity of the zones assessed, that the user can if desired override the program sequence, e.g. to reassess doubtful zones, register non-assessability of the test object under scrutiny, or to dispense with the check facility. It is also possible to provide additional data-processing facility, so that the assessment data in respect of a test object can be used to give, for example, a visible output of further useful information, such as the identity of a substance or micro-organism, or a minimum inhibitory concentration of a pharmaceutical for a micro-organism under test.

It will be seen that in this form of the invention, the tasks demanded of a user in performing a visual assessment of a test object can be reduced in complexity to the following: a start-up operation involving inserting a test object in position, switching on, and possibly selecting a suitable one of a plurality of programs to aid the assessment of the particular type of test object in hand; an assessment operation, involving sequentially assessing each zone selectively illuminated, making an input of data corresponding to the assessment, null-difference checking the resulting visible reproduction or diagram of the condition assessed, and registering acceptance of the check; and whenever required a readout operation involving extracting the assessment data or any data-processing derivative thereof, in any chosen convenient form.

Of course the form in which the user makes the input of data corresponding to an assessment, or in which he/she registers acceptance of the check, can be fixed in any convenient way, for example by prescribing appropriate codes for entry on a typewriter-type or other keyboard input.

This arrangement for assessing test objects has advantages in minimising user failure and fatigue, because it provides means to protect against error production due either to assessment of a wrong zone, or to wrong assessment of a zone. This can be particularly important where a large number of test objects to be assessed each contain a large number of zones, e.g. up to about a hundred or more, each capable of exhibiting any one of a number of visible states. These would become difficult to assess reliably, especially in large numbers, when the operator becomes fatigued and at the same time to pay attention to multiple matters, such as registering the correct zone, recording the results manually, and possibly also checking the assessment by comparing unlike visible objects in the comparison of which a mental act of interpretation is necessary. These are conditions which encourage operator error, and in protecting against such error the invention usefully contributes to the means available for improving the reliability of test results which can have important consequences, e.g. in the therapy of patients or the safe conduct of manufacturing processes.

An embodiment of the invention is particularly described by way of non-limitative example.

This example is an arrangement to assist assessment of a test object which comprises a transparent plastics tray having an array of twelve columns and in each a row of eight wells. Each column of wells contains a series of dilutions of a selected pharmaceutical in which samples of a micro-organism, e.g. from a patient with an infection, have been incubated. It will normally happen that growth and turbidity is seen in each column up to a limiting concentration of the pharmaceutical. The operator's task may then be to register where the limit occurs in each column, and to provide interpretation in terms of minimum inhibitory concentration.

This task can be assested by placing the tray upon a transparent plastics plate marked with a grid of $9 \times 13$ lines delimiting $8 \times 12$ square zones each in registration with a well. At each corner of each square zone is a small spotlight source, in this case a light-emitting diode or the end of a fine fibre-optic conductor with such a diode at its other end. The arrangement is such that the operator has enough background light to see the the state of each well, whether transparent or turbid. A viewer is provided so that this operator sees the plate by either direct or reflected light from the plate.

Each light source is individually addressable by a small computer also linked to a visual display unit and an operator input keyboard.

The computer is programmed to control the following operations. The four corners of each square constituting a column for assessment are selectively illuminated under control of the program, drawing the operator's attention. Upon receipt of a data input from the operator corresponding to assessment of the illuminated column, the program controls the production of a display showing in diagrammatic form the visible condition corresponding to the assessment data input made. Upon receipt of an operator input registering confirmation that the display corresponds visibly to the test zone under scrutiny, the program controls storage of the assessment data and moves on to produce a similar operating sequence for all the other relevant test zones. At the end of the assessment of the tray the data are read out or stored as desired.

It is noted that the null-difference check display presented to the operator can be shown either on a visual display unit of a kind normally associated with a computer, and/or by lighting-up of an appropriate pattern of the selectively controllable light sources. The check displays can be shown either at the conclusion of an individual reading and entering operation and/or at the conclusion of the operations of reading the whole test object.

FIG. 1 of the accompanying diagrammatic drawings shows in diagrammatic form a selective illumination means for applying the invention to the reading of microtitre wells having eight rows and twelve columns of wells, for example. It takes the form of a rectangular translucent plate (boundary not shown) with an inlaid rectangular gridwork of horizontal lines 1 and vertical lines 2. Light sources are arranged at each intersection such as 3, and indicator lamps are provided for rows A–H and columns 1–12. Registration ridges or other retainers are provided so that a translucent microtitre plate can be placed with its wells lying between the intersections. FIG. 1 shows diagrammatically the state of illumination for a reading required of well E8: indicator lamps E and 8 are lit and the four intersection light sources adjacent to the well to be read are also lit. The electrical wiring for energizing the lighting and control can conveniently be let into grooves along the gridlines of the plate, e.g. a glass or plastics plate, and sealed in place with suitable material such as resin filler, so that the embedded light sources can still light up visibly.

The microtitre plate can be located on the grid by visual registration of the wells with the grid interstices, or by the help of ridges or grooves at the edges of the grid, or by any equivalent positive location means. Background illumination is useful with the embodiment shown diagrammatically in FIG. 1, and can be provided by either a mirror and daylight arranged so that the plate placed on the grid is viewed against daylight background, or by artificial lighting and, if needed, any suitable diffuser means, e.g. a diffuser plate behind the plate and grid.

Figure 2:
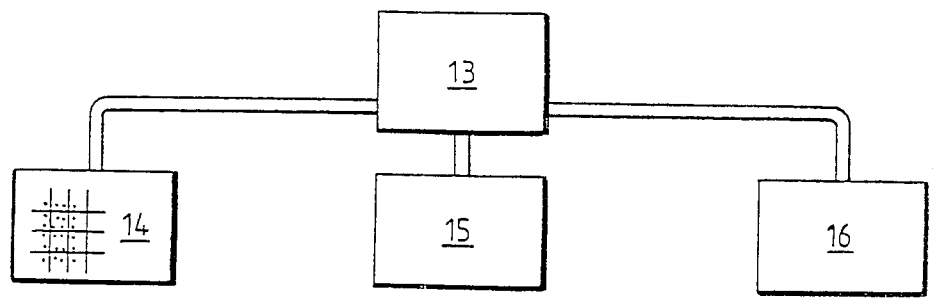

FIG. 2 of the accompanying diagrammatic drawings is a block diagram showing the basic scheme of interconnection of the selective illuminator of FIG. 1, the control means, the manual actuation means and the display unit. The details of the interconnections follow normal electronic practice and in themselves form no part of the invention. Control means 13 can for example take the form of a commercially available microcomputer equipped with peripheral ports and programmed to control and/or respond to the selective illumination means 14, a keyboard or other data input device 15 actuatable by the operator, and a display unit 16. A separate display unit can be dispensed with, if for example the selective illumination means is used to form the check display. Alternatively a check display can be formed on either or both of the selective illumination means and a separate display unit, at will.

Operation of the device for assisting the visual assessment of a microtitre plate can be as follows. The operator first places the microtitre plate in registration with the selective illumination means, then starts the control program. The control program causes indicative illumination of the first test zone to be assessed, in the way described above. The operator assesses the zone visually, and makes an input corresponding to the assessment, entering it at the data input keyboard. A check display may be formed at this point, in which case the operator can make any required correcting input by appropriate keyboard actuation.

Upon suitable stepping actuation by the operator, or after a preset time delay, the control program then moves on to repeat the cycle with the next test zone to be assessed. Finally a check display can be formed to show the assessment of the whole plate.

The data corresponding to the plate assessment can then be stored, further processed, printed out, etc., in any desired manner which can be arranged by conventional programming techniques not in themselves constituting part of the invention. For example, the data processing can include automatic comparison of the plate data with reference data stored in the microcomputer, so as to produce a useful interpreted output. Standard published data for the interpretation of the microtitre plates or other test objects can in such a case be stored in the computer and used as basis for comparison by techniques known in themselves. These or other reference data can also be used to present the operator with a visual display of reference data appropriate to guide the assessment of the test location currently under scrutiny, e.g. a list of possible visual conditions of the test location, and their significance.

It can be seen that this apparatus and its use enable the tedious and error-prone process of checking and interpretation of microtitre plates and other test objects to be carried out with speed and reliability, and offer an opportunity to store and process the results electronically without further intervention by an operator. This also allows both short and long term data-storage, analysis and presentation in composite printed form.

We claim:

1. Apparatus for use in and for assisting the visual assessment by a human operator of test objects, in each of which test objects a multiplicity of test locations each has one or more visible characteristics capable of exhibiting any one of a number of conditions to be assessed, the apparatus comprising:
   (a) means for positively locating the test object in registration with selective illuminating means;
   (b) means for illuminating selected test locations of the test object;
   (c) means for controlling the illuminating means so that the test locations can be selectively illuminated either singly or in groups, according to a program-determined sequence;
   (d) means to enable the operator manually to actuate and control stepping along the sequence;
   (e) means arranged for actuation by the operator for recording and storing data input corresponding to the operator's visual assessment of the selectively illuminated location or locations; and
   (f) means for presenting to the operator a visual check display corresponding to the data input recorded in respect to the test locations under illumination to enable the operator to check the correctness of the data recorded by visually comparing the display with the test location, said apparatus comprising a two-dimensional array of test locations, in which illuminating means (a) includes means for producing, at each step of the sequence, a mark or pattern of marks, adjacent to the test location or locations to be assessed, against a back-ground of general illumination derived either by admission of daylight or from a diffuse light source.

2. Apparatus according to claim 1, for assisting the visual assessment of a test object comprising a two-dimensional array of test locations, in which illuminating means (a) includes means for producing, at each step of the sequence, a dot or line, or pattern of dots or lines, adjacent to the test location or locations to be assessed, against a back-ground of general illumination derived either by admission of daylight or from a diffuse light source.

3. Apparatus according to claim 1 or 2, in which means (f) for presenting the visual check display to the operator includes means to form the check display on the selective illumination means (b).

4. Apparatus according to claim 1 or 2 further comprising means for presenting the operator with a visual display of reference data appropriate to guide the assessment of the selectively illuminated test location.

5. The combination of apparatus according to claim 1 or 2 with a test object as referred to.

6. A combination of apparatus and test object according to claim 5, in which the test object is a prepared microtitre plate or tray having a rectangular array of reaction zones or wells in which a plurality of microbial culture preparations or of biological or chemical test preparations has been produced.

* * * * *